United States Patent
Han

(10) Patent No.: US 7,200,311 B1
(45) Date of Patent: Apr. 3, 2007

(54) SURFACE CORRUGATION ON INTERNAL REFLECTION INFRARED WAVEGUIDE FOR ENHANCED DETECTION SENSITIVITY AND SELECTIVITY

(75) Inventor: Sang Han, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 5 days.

(21) Appl. No.: 11/101,465

(22) Filed: Apr. 8, 2005

Related U.S. Application Data

(60) Provisional application No. 60/560,670, filed on Apr. 8, 2004.

(51) Int. Cl.
*G02B 6/10* (2006.01)

(52) U.S. Cl. .................................. 385/129; 385/132

(58) Field of Classification Search ........ 385/129–132, 385/116, 121, 147
See application file for complete search history.

(56) References Cited

U.S. PATENT DOCUMENTS

2002/0125589 A1* 9/2002 Katzir ........................ 264/1.23
2005/0214167 A1* 9/2005 Archibald et al. ......... 422/68.1

OTHER PUBLICATIONS

Sang M. Han and Eray S. Aydil, Structure and chemical composition of fluorinated $SiO_2$ films deposited using $SiF_4/O_2$ plasmas, Nov./Dec. 1997, pp. 2893-2904, Department of Chemical Engineering, University of California Santa Barbara California 93106, USA.

Sang M. Han and Eray S. Aydil, Study of surface reactions during plasma enhanced chemical vapor deposition of $SiO_2$ from $SiH_4$, $O_2$, and Ar plasma. Jul./Aug. 1996, pp. 2062-2070, Department of Chemical Engineering, University of California Santa Barbara California 93106, USA.

Sang M. Han and Eray S. Aydil, Plasma and surface diagnostics during plasma-enhanced chemical vapor deposition of $SiO_2$ from $_4/O_2/$ Ar discharges, 1996, The Solid Films 290-291 pp. 427-434, Department of Chemical Engineering, University of California Santa Barbara California 93106, USA, no month.

Sang M. Han and Eray S. Aydil, Detection of Combinative infrared absorption bands in thin silicon dioxide films, Jun. 16, 1997, American Institute of Physics pp. 3269-3271, Department of Chemical Engineering, University of California Santa Barbara California 93106, USA.

Y.J. Chabal, High-Resolution Infrared Spectroscopy of Adsorbates on Semiconductor Surfaces: Hydrogen on Si(100) and Ge(100), Jul. 3, 1985, pp. 594-608, At&T Bell Laboratories, Murray Hill, New Jersey 07974, USA, Elsevier Science Publishers B.V.

(Continued)

*Primary Examiner*—Kevin S. Wood
(74) *Attorney, Agent, or Firm*—MH2 Technology Law Group

(57) ABSTRACT

Internal reflection infrared waveguides having enhanced surface sensitivity and methods for using them are provided. In various embodiments, the internal reflection infrared waveguides can include a multiple internal reflection (MIR) crystal that is substantially transparent to mid-infrared light. The top surface of the MIR crystal can further include a plurality of nanochannels that extend from the top surface of the MIR crystal into the MIR crystal.

19 Claims, 4 Drawing Sheets

OTHER PUBLICATIONS

Sang M. Han and Eray S. Aydil, Silanol Concentration Depth Profiling during Plasma Deposition of $SiO_2$ Using Multiple Internal Reflection Infrared Spectroscopy, Nov. 1997, The Electrochemical Society, Inc, pp. 3963-3967, Department of Chemical Engineering, University of California Santa Barbara California 93106, USA.

Sang M. Han and Eray S. Aydil, Reasons for lower dielectric constant of fluorinated $SiO_2$ films, Feb. 15, 1998, Journal of Applied Physics, vol. 83, No. 4, pp. 2172-21778, Department of Chemical Engineering, University of California Santa Barbara California 93106, USA.

Eray S. Aydil, Zhen H. Zhou, Richard A. Gottscho and Yves J. Chabal, Real Time in situ monitoring of surfaces during glow discharge processing $NH_3$ and $H_2$ plasma passivation of GaAs, Dec. 10, 1994, American Vacuum Society 1998, pp. 258-267, At&T Bell Laboratories, Murray Hill, New Jersey 07974, USA.

Andrew D. Bailey III and Richard A. Gottscho, Real-Time Monitoring of Silicon Nitride Composition During Plasma Enhanced Chemical Vapor Deposition, Jan. 21, 1995, Jpn. J. Appl. Phys. vol. 34 (1995), pp. 2172-2181, Part 1, No. 4B, Apr. 1995, At&T Bell Laboratories, Murray Hill, New Jersey 07974, USA.

Francis M. Mirabella, Jr, Internal Reflection Spectroscopy Theory and Applications, Practical Spectroscopy Series vol. 15, 1993, Marcel Decker, Inc. 270 Madison Avenue, New York, NY 10016 USA, no month.

* cited by examiner

SURFACE CORRUGATION ON INTERNAL REFLECTION INFRARED WAVEGUIDE FOR ENHANCED DETECTION SENSITIVITY AND SELECTIVITY

CROSS-REFERENCE TO RELATED APPLICATIONS

This application claims priority to U.S. Provisional Patent Application Ser. No. 60/560,670 filed on Apr. 8, 2004, the disclosure of which is incorporated in its entirety by reference herein.

FIELD OF THE INVENTION

The present invention relates to infrared waveguides and, more particularly, relates to multiple internal reflection crystals with enhanced sensitivity.

BACKGROUND OF THE INVENTION

Internal reflection infrared waveguides have been widely used to probe interfacial phenomena of semiconductor, insulator, and organic films. For example, conventional internal reflection infrared waveguides that include an attenuated total reflection (ATR) crystal have been used to probe the surfaces of semiconductor and insulator materials. As shown in FIG. 1, a film 30 is disposed on a smooth top surface of a trapezoidal ATR crystal 20. Generally, an infrared beam 10 enters one side of trapezoidal ATR crystal 20 and makes a number of total internal reflections from the top and bottom surface. Beam 10 then exits from the other side of trapezoidal ATR crystal 20. To exit the trapezoidal ATR crystal 20, the incident angle of beam 10 on the top and bottom surfaces should exceed the critical angle ($\theta_c$), which is defined by:

$$\theta_c = \sin^{-1}(n_3/n_1)$$

where $n_1$ is the refractive index of the optically denser ATR crystal. Further, $n_3$ is the refractive index of a less dense medium surrounding film 30, such as, for example, air.

Upon total reflection at the smooth top surface of trapezoidal ATR crystal 20, an evanescent electric field E(z) is created that permeates into film 30 and interacts with infrared active species on and in film 30. Each reflection from the top surface of trapezoidal ATR crystal 20 adds to the infrared absorbance. This results in sub-monolayer detection sensitivity of surface adsorbates. The enhanced infrared absorbance can be converted to fractional coverage of a monolayer when properly calibrated. For a typical infrared range from 5000 to 450 $cm^{-1}$, the depth of penetration for the evanescent electric field ranges from 0.2 to 1.5 μm, depending on the infrared wavenumber.

Internal reflection infrared waveguides can potentially be useful for a variety of commercial applications, such as, for example, incorporation into semiconductor manufacturing, micro-electromechanical systems (MEMS) manufacturing, and integrated biosensor manufacturing. Another promising commercial application is as diagnostic tools for real time probing of interfacial phenomena during processing of nanostructures and nanodevices. Realization of these applications, however, requires increased surface sensitivity without significant loss of infrared throughput.

Thus, there is a need to overcome these and other problems of the prior art to provide internal reflection infrared waveguides with enhanced surface sensitivity and methods for their use.

SUMMARY OF THE INVENTION

According to various embodiments, the present teachings include an infrared waveguide including a multiple internal reflection (MIR) crystal having a top surface, wherein the MIR crystal is substantially transparent to mid-infrared light. The top surface of the MIR crystal can further include a plurality of nanochannels, wherein each of the plurality of nanochannels extends from the top surface into the MIR crystal.

According to various embodiments, the present teachings include an infrared waveguide including an attenuated total-internal reflection (ATR) crystal having a first material having an index of refraction n. The infrared waveguide can further include a plurality of channels disposed on a top surface of the ATR crystal, wherein the plurality of channels are formed of a second material having an index of refraction substantially similar to n.

According to various embodiments, the present teachings include a method of detecting an infrared active material. The method includes providing an MIR crystal including a plurality of nanochannels on a top surface of the MIR crystal, wherein each of the plurality of nanochannels extends from the top surface into the MIR crystal. The method further can include providing a solution comprising an infrared light absorbing active material in the plurality of nanochannels and directing an infrared light to enter a first side of the MIR crystal such that the infrared light reflects more than once from the top surface of the MIR crystal. The method can further include detecting the infrared light after the infrared light exits from a second side of the MIR crystal to determine infrared absorbance from the infrared light absorbing materials.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

In the following description, reference is made to the accompanying drawings that form a part thereof, and in which are shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

As used herein, the term "attenuated total reflection crystal" is synonymous and used interchangeably with "ATR crystal," "multiple internal reflection crystal," and "MIR crystal."

FIGS. 2–7 depict exemplary embodiments of internal reflection infrared waveguides including an MIR crystal with surface corrugations. The exemplary embodiments can provide increased surface sensitivity over conventional smooth surface ATR crystals without sacrificing infrared throughput.

Figure 1:
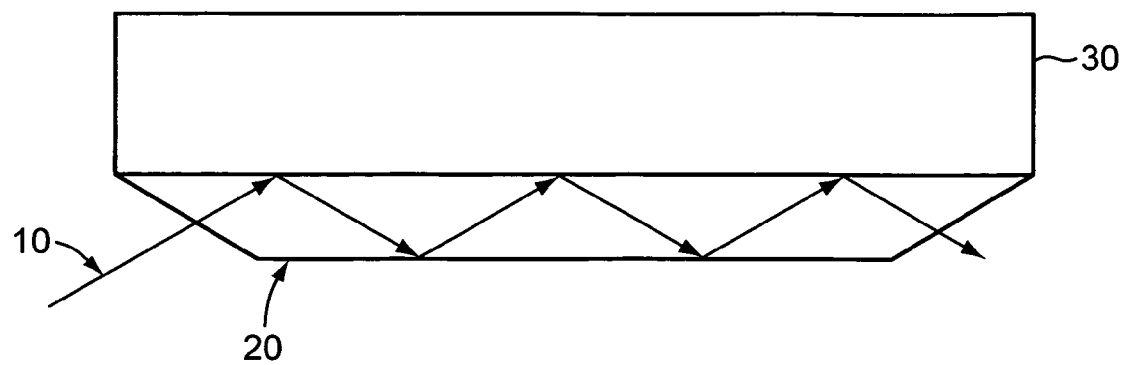
FIG. 1 depicts a conventional internal reflection infrared waveguide.
Figure 2A:
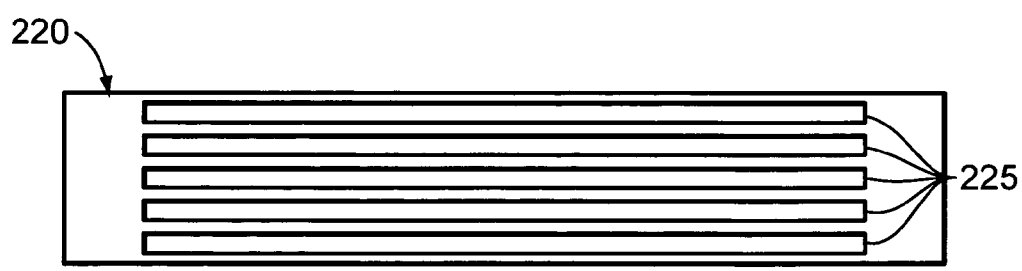
FIG. 2A depicts a top view of a multiple internal reflection (MIR) crystal including a plurality of corrugations in accordance with exemplary embodiments of the present teachings.
Figure 2B:
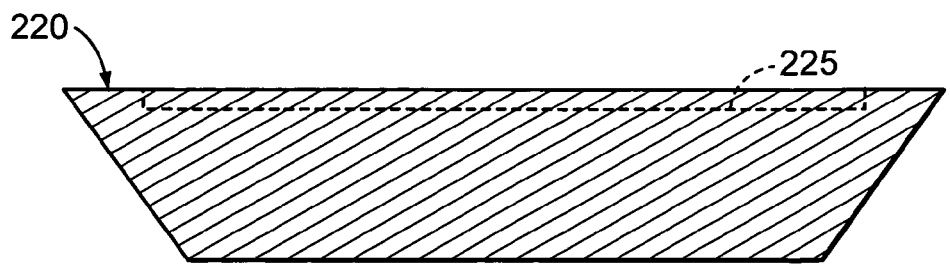
FIG. 2B depicts a side view of an MIR crystal including a plurality of corrugations in accordance with exemplary embodiments of the present teachings.

FIGS. 2A and 2B depict an exemplary embodiment of an MIR crystal 220 including surface corrugations. MIR crystal 220 can be formed of a material that is transparent to at least a portion of mid-infrared light (about 2.5 to about 16 μm), such as, for example, Si, Ge, GaAs, ZnS, ZnSe, and KRS-5. The shape of MIR crystal 220 can be, for example, a trapezoid or a parallelogram. The dimensions of MIR crystal 220 can vary as will be discussed below.

Figure 3:
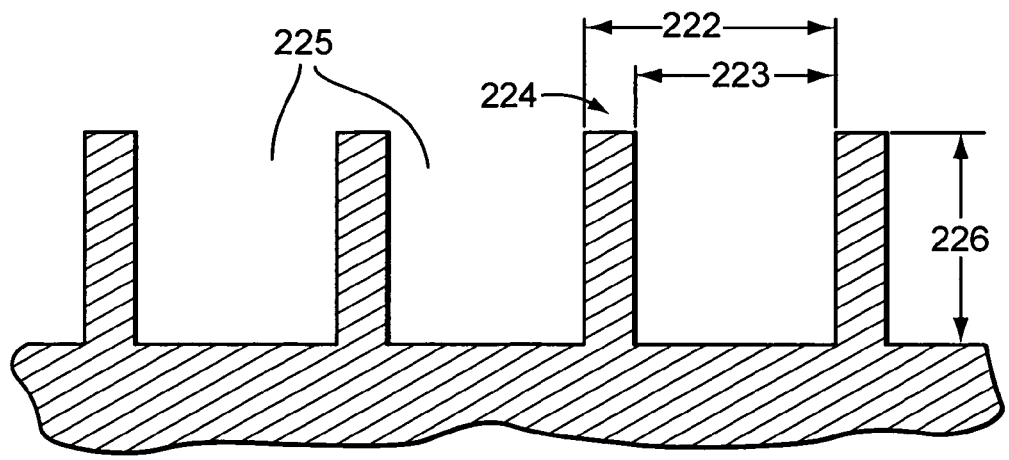
FIG. 3 depicts a magnified partial view of corrugations on a top surface of an MIR crystal in accordance with exemplary embodiments of the present teachings.

FIG. 2A shows an MIR crystal 220 that can include surface corrugations, such as, for example, a plurality of nanochannels 225. Nanochannels 225 can be formed on a top surface of MIR crystal 220 and can extend into the top surface as shown in FIG. 2B. In various embodiments, rectangular nanochannels, as shown in FIGS. 2A, 2B, and 3 can provide clearer information about adspecies. For instance, rectangular nanochannels can enable adspecies on the sidewalls with dipole moments perpendicular to the sidewalls to be distinguished from adspecies on the trench bottom with dipole moments perpendicular to the trench bottom. That is, polarized infrared light can be used to extract orientational information of molecules on the nanochannel sidewalls versus on the nanochannel bottom. Nanochannels 225, however, can be any shape if orientation information is not desired.

Nanochannels 225 can be formed by, for example, etching. According to various embodiments, nanochannels 225 can be formed by plasma etching using, for example, a fluorocarbon plasma, a $Cl_2$/HBr plasma, or an He/$SF_6$ plasma. In various embodiments, a mask can be developed by interferometric lithography on a top surface of MIR crystal 220. Nanochannels 225 can then be formed by etching. The mask can be removed using, for example, an organic solvent.

Referring to FIG. 3, nanochannels 225 can have a pitch (p) 222, a nanochannel top width ($L_1$) 224, a nanochannel bottom width ($L_2$) 223, and a nanochannel depth (d) 226. Pitch 222 is a sum of nanochannel top width 224 and nanochannel bottom width 223 and indicates the density of nanochannels per unit area. For example, finer pitch and deeper channels can increase the surface area of the MIR crystal by a factor of $f_A$, where $f_A$ is defined by:

$$f_A = c_{corr}\frac{(2d + p)}{p} + c_{flat} \qquad (1)$$

where $c_{corr}$ is the fraction of the top surface of the MIR crystal that is corrugated surface and $c_{flat}$ is the fraction of the top surface of the MIR crystal that is flat. As shown by Equation 1, decreasing pitch 222 and increasing depth 226 can increase $f_A$. According to various embodiments, increasing $f_A$ can increase the sensitivity of MIR crystal 220 by improving, for example, the infrared absorbance of characteristic vibrational modes of molecules adsorbing on the corrugated surface. Therefore, in various embodiments, $L_1$ (224) can be less than $L_2$ (223). According to various embodiments, $c_{flat}$ can be less than 1. Further, according to various embodiments, nanochannel bottom width $L_2$ (223) can be 250 nm or less. Still further, according to various embodiments, nanochannels 225 can have an aspect ratio greater than zero.

Figure 4:
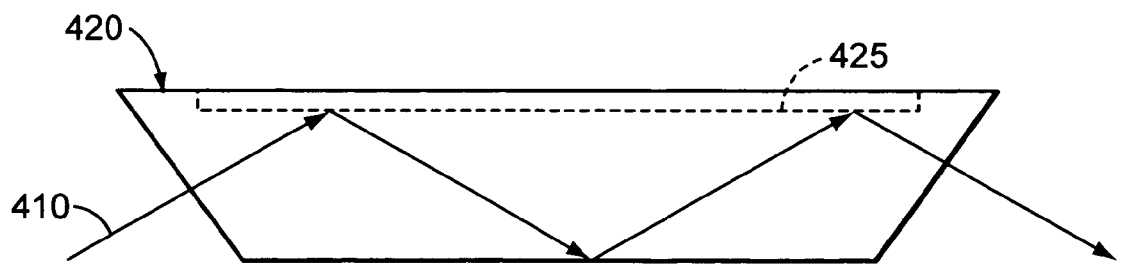
FIG. 4 depicts multiple total internal reflections of an infrared light within an MIR crystal in accordance with exemplary embodiments of the present teachings.

In various embodiments, enhanced detection of surface adsorbates can be accomplished using MIR crystal 420, as shown in FIG. 4. MIR crystal 420 can include a plurality of nanochannels 425 that contain infrared active molecules adsorbing on the surface of nanochannels 425. An infrared light 410 from a light source (not shown) can enter one side of a trapezoidal MIR crystal 420. Infrared light 410 can make one or more total internal reflections from the corrugated surface of MIR crystal 420 before exiting a second side of MIR crystal 420. Thus, the dimensions of MIR crystal can vary such that one or more total internal reflections can occur from the corrugated surface of the MIR crystal. After exiting, infrared light 410 can be directed towards a detector (not shown) to determine, for example, infrared absorbance.

Figure 5:
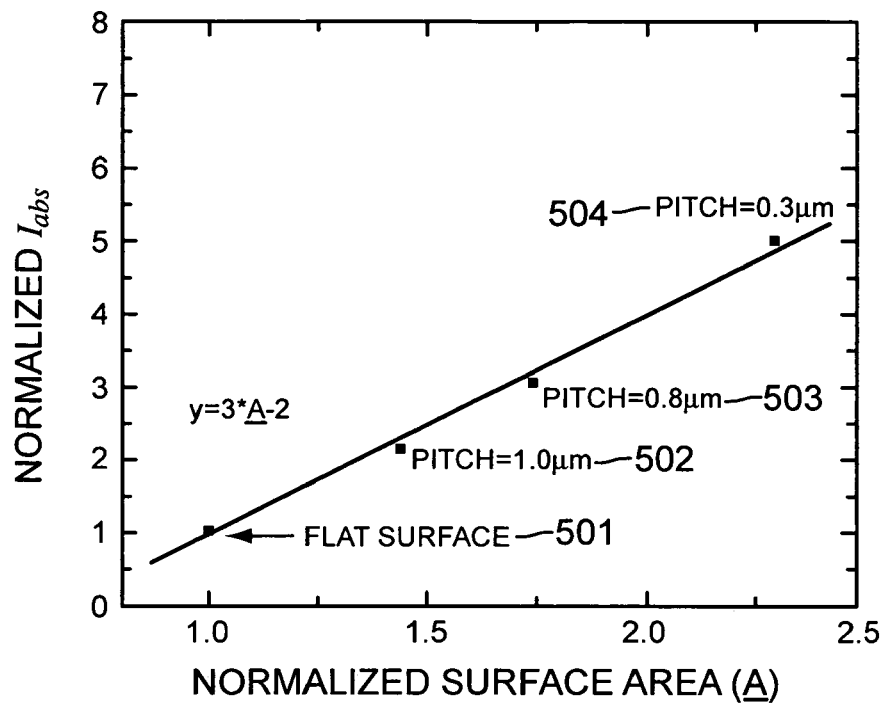
FIG. 5 is a graph showing normalized integrated absorbance as a function of decreasing corrugation pitch in accordance with exemplary embodiments of the present teachings.

Enhanced sensitivity provided by corrugation is shown in FIG. 5. FIG. 5 shows that the integrated absorbance of asymmetric and symmetric C—H stretching vibrational modes of a hexadecanethiolate self-assembled monolayer on a Ge MIR crystal increased linearly with increasing corrugation. In this example, the integrated absorbance increased from a value represented by 501 for the Ge MIR crystal with a smooth top surface to a value represented by 502 for a Ge MIR crystal with nanochannels having a pitch of 1.0 µm. Moreover, the integrated absorbance continued to increase as the pitch was decreased to 0.8 µm (503) and then to 0.3 µm (504). While not intending to be limited to any particular physical theory, it is believed that the enhanced absorbance may be due to more than the increased surface area provide by the corrugations, such as the nanochannels. The enhanced absorbance may also be due to the existence of the evanescent electromagnetic field, which extends from the channel bottom and whose magnitude is the largest at the channel bottom. That is, infrared light 410 traversing MIR crystal 420 may reflect from the nanochannel bottom. Thus, when $L_1 \ll L_2$, the overlap of evanescent electromagnetic waves from neighboring channel bottoms may give rise to enhanced electric field strength and stronger coupling between the dipole moments of infrared-active molecules and the electric field.

In various embodiments, the infrared-active species detected by the MIR crystal with surface corrugations can comprise biomolecules, such as, for example proteins, DNA, organelle, and lipid bilayers that comprise plant and/or animals material. Further, the corrugations comprising nanochannels can be used to orient anisotropically shaped biomolecules. In still other embodiments, the nanochannels can be used for real time monitoring of molecular transport within the nanochannels.

Figure 6:
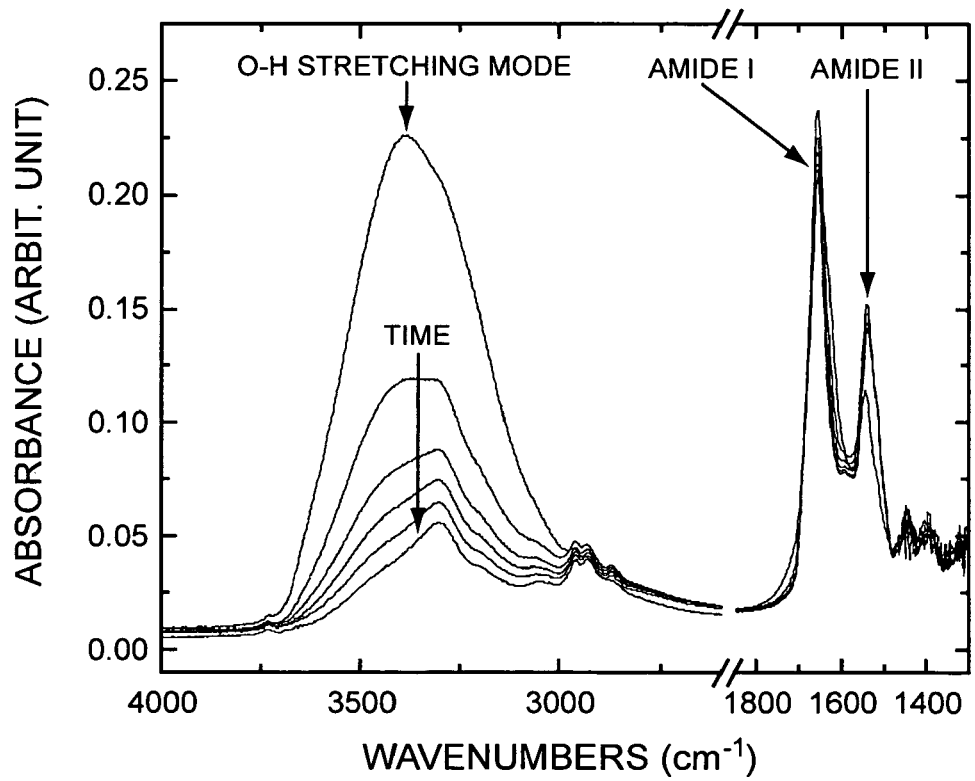
FIG. 6 is a graph showing infrared absorbance of bovine serum albumin detected by nanomachined-waveguide-assisted Fourier Transform Infrared Spectroscopy (NWA-FT-IRS) in accordance with exemplary embodiments of the present teachings.

In an exemplary embodiment, infrared absorbance of bovine serum albumin was detected by NWA-FTIRS. In this example, the MWA-FTIRS device included a trapezoidally shaped Ge MIR crystal with corrugations in the top surface. The corrugations comprised nanochannels 100 nm wide and 200 nm deep, at a 300 nm pitch. A Pyrex plate was anodically bonded to the corrugated surface of the MIR crystal to form a top wall for each of the plurality of nanochannels. Bovine serum albumin in a buffered saline solution at a concentration of 1 mg/mL was injected in to the nanochannels via capillary action. FIG. 6 shows the detected absorbance in arbitrary units as a function of wavenumber in $cm^{-1}$. As shown in FIG. 6, the O—H stretching vibrational mode of $H_2O$ in the buffered saline solution near 3400 $cm^{-1}$ decreased with time as evaporation occurred. The Amide I and II regions, however, remained relatively constant during the same time. FIG. 5 further shows that the bending mode of $H_2O$ near 1596 $cm^{-1}$ was suppressed in the nanochannels. In contrast to an MIR crystal without corrugations, minimal interference from $H_2O$ modes provided improved reliability when using Amide I and II for the purpose of determining protein structure and orientation.

Figure 7A:
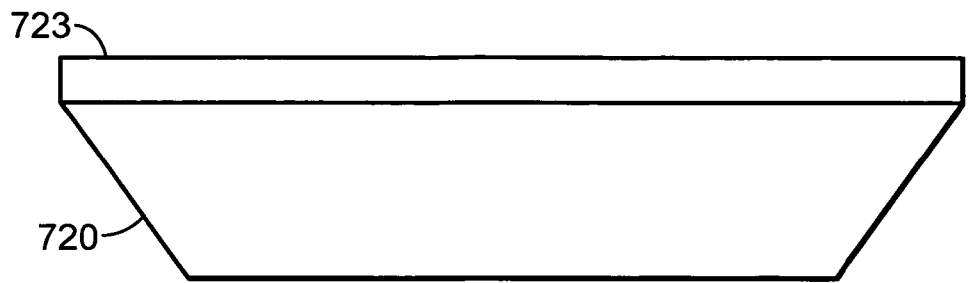
FIG. 7A is a side view of an MIR crystal with a deposited layer on the top surface of the MIR crystal in accordance with exemplary embodiments of the present teachings.
Figure 7B:
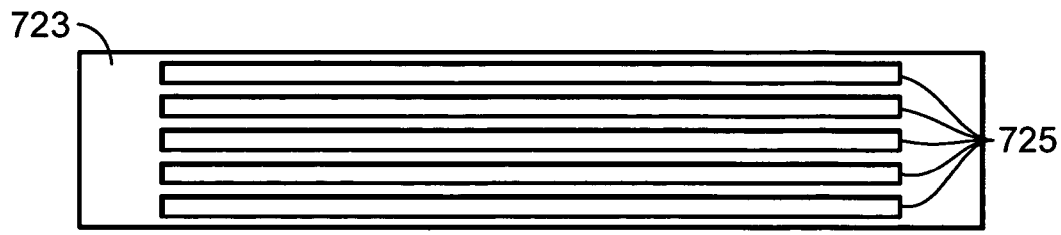
FIG. 7B is a top view of an MIR crystal including a plurality of nanochannels in accordance with exemplary embodiments of the present teachings.
Figure 7C:
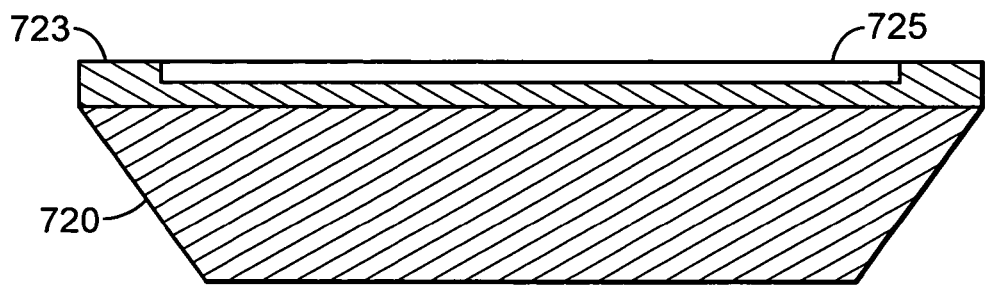
FIG. 7C is a cross sectional view of an MIR crystal including a plurality of nanochannels in accordance with exemplary embodiments of the present teachings.
Figure 7D:
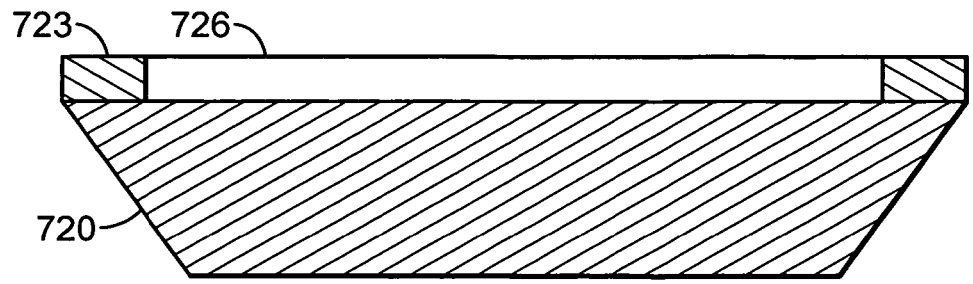
FIG. 7D is a cross sectional view of another MIR crystal including a plurality of nanochannels in accordance with exemplary embodiments of the present teachings.

According to various embodiments, a corrugated layer can be formed from a layer deposited on an MIR crystal. FIG. 7A shows a side view of an MIR crystal 720 and a deposited layer 723. An index of refraction of deposited layer 723 can be substantially similar to an index of refraction n of MIR crystal 720. As used herein, the term "substantially similar" with reference to "refractive index" means that the angle of incidence of infrared light to the deposited layer does not exceed the critical angle, such that the infrared light travels through the deposited layer and undergoes total internal reflection only when the infrared light reaches the top surface of the deposited layer. In an exemplary embodiment, MIR crystal 720 can comprise Ge and deposited layer 723 can comprise amorphous hydrogenated Ge (a-Ge:H). In various other embodiments, layer 723 can comprise, for example, a-SiGe:H or a-Si:H. Deposited layer 723 can be deposited, for example, using a $GeH_4/Ar$ plasma to a thickness of about 1 µm. Referring to the top view of FIG. 7B, corrugations can then be formed in deposited layer 723 using a plasma, such as, for example, a fluorocarbon plasma, a $Cl_2/HBr$ plasma, or an $He/SF_6$ plasma, and a photomask to etch a plurality of nanochannels 725. Plurality of nanochannels 725 can have, for example, a width of less than 1 µm and an aspect ratio greater than zero.

In various embodiments, the depth of nanochannels 725 can be less than the thickness of deposited layer 723. As shown in the cross sectional view of FIG. 7C, the bottom and sidewalls of each of the plurality of nanochannels 725 can be formed by the material comprising deposited layer 723.

In various other embodiments, a plurality of nanochannels 726 can be formed by etching layer 723 to expose portions of the top surface of MIR crystal 720. In this manner, the top surface of MIR crystal 720 can form the bottom of each of the plurality of nanochannels 726, as shown, for example in the cross sectional view of FIG. 7D. Because the material forming the nanochannel sidewalls can be different than the material forming the nanochannel bottom, MIR crystal 720, including the plurality of nanochannels 726, can be used to distinguish molecules adsorbing on the nanochannel sidewall from molecules adsorbing on the nanochannel bottom. For example, using a p-polarized infrared light that has a field component (Ex) parallel to the top surface of MIR crystal 720 and a field component (Ez) perpendicular to the top surface of the MIR crystal, molecules that have a chemical affinity towards the sidewall of nanochannels 726 compared with the bottom of nanochannels 726 (i.e., the exposed surface of 720) can be preferentially isolated and detected.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising."

As used herein, the term "one or more of" with respect to a listing of items such as, for example, A and B, means A alone, B alone, or A and B.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An infrared waveguide for enhanced surface sensitivity comprising:
   a multiple internal reflection (MIR) crystal comprising a top surface, wherein the MIR crystal comprises a material that is substantially transparent to mid-infrared light; and
   a plurality of nanochannels sized to enhance sensitivity to surface adsorbates, wherein each of the plurality of nanochannels extends from the top surface of the MIR crystal into the MIR crystal.

2. The infrared waveguide of claim 1, wherein a fraction of the top surface not having channels ($c_{flat}$) is less than 1.

3. The infrared waveguide of claim 1, wherein a cross-section of each of the plurality of nanochannels has a rectangular shape.

4. The infrared waveguide of claim 1, wherein each of the plurality of nanochannels has a width of about 250 nm or less.

5. The infrared waveguide of claim 1, wherein each of the plurality of channels is separated by a section of the multiple internal reflection crystal such that a width of each of the plurality of channels is greater than the section of the multiple internal reflection crystal.

6. The infrared waveguide of claim 1, wherein the MIR crystal comprises one of Si, Ge, GaAs, ZnS, ZnSe, and KRS-5.

7. A Fourier Transform Infrared Spectroscopy device (FTIR) comprising:
the infrared waveguide of claim 1, wherein each of the plurality of nanochannels further comprises:
a top wall;
an infrared light source; and
an infrared light detector.

8. The infrared waveguide of claim 1, wherein a shape of the MIR crystal is at least one of a trapezoid and a parallelogram.

9. An infrared waveguide comprising:
an attenuated total-internal reflection (ATR) crystal comprising a first material having an index of refraction n; and
a plurality of channels disposed on a top surface of the ATR crystal, wherein the plurality of channels are formed of a second material having an index of refraction substantially similar to n, and wherein the plurality of channels are sized to enhance sensitivity to surface adsorbates.

10. The infrared waveguide of claim 9, wherein a bottom of each of the plurality of channels is formed by the second material.

11. The infrared waveguide of claim 9, wherein a bottom of each of the plurality of channels is formed by the top surface of the ATR crystal.

12. The infrared waveguide of claim 9, wherein a shape of the ATR crystal is at least one of a trapezoid and a parallelogram.

13. The infrared waveguide of claim 9, wherein the ATR crystal comprises a material substantially transparent to infrared light.

14. The infrared waveguide of claim 9, wherein each of the plurality of channels has a width of about 250 nm or less and an aspect ratio greater than zero.

15. A method of detecting an infrared active material comprising:
providing an MIR crystal comprising a plurality of nanochannels sized to enhance sensitivity to the infrared active material, wherein each of the plurality of nanochannels extends from the top surface of the MIR crystal into the MIR crystal;
providing a solution comprising an infrared light absorbing active material in the plurality of nanochannels;
directing an infrared light to enter a first side of the MIR crystal such that the infrared light reflects more than once from the top surface of the MIR crystal; and
detecting the infrared light after the infrared light exits from a second side of the MIR crystal to determine infrared absorbance from the infrared light absorbing materials.

16. The method of claim 15, further comprising determining infrared absorbance as a function of wavenumber.

17. The method of claim 16, wherein the infrared light absorbing active materials comprise biomolecules.

18. The method of claim 16, wherein the step of providing a solution comprising infrared light absorbing active materials in the plurality of nanochannels comprises injecting a liquid containing the biomolecules into the nanochannels.

19. The method of claim 16, wherein the step of detecting the infrared light after the infrared light exits a second side of the MIR crystal to determine infrared absorbance comprises using Fourier Transform Infrared Spectroscopy (FT-IRS) to determine infrared absorbance.

* * * * *